(12) United States Patent
Zhu et al.

(10) Patent No.: US 11,639,352 B2
(45) Date of Patent: May 2, 2023

(54) BENZOTHIAZOLE COMPOUNDS FOR THE TREATMENT OF AUTOIMMUNE DISEASES

(71) Applicant: Hoffmann-La Roche Inc., Little Falls, NJ (US)

(72) Inventors: Wei Zhu, Shanghai (CN); Ge Zou, Shanghai (CN); Fabian Dey, Basel (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 121 days.

(21) Appl. No.: 17/273,659

(22) PCT Filed: Sep. 4, 2018

(86) PCT No.: PCT/EP2018/073648
§ 371 (c)(1),
(2) Date: Mar. 4, 2021

(87) PCT Pub. No.: WO2020/048583
PCT Pub. Date: Mar. 12, 2020

(65) Prior Publication Data
US 2021/0340136 A1 Nov. 4, 2021

(51) Int. Cl.
| C07D 413/14 | (2006.01) |
| A61K 31/5377 | (2006.01) |
| C07D 417/14 | (2006.01) |
| C07D 417/04 | (2006.01) |
| C07D 471/08 | (2006.01) |
| C07D 471/10 | (2006.01) |

(52) U.S. Cl.
CPC ......... C07D 417/14 (2013.01); C07D 417/04 (2013.01); C07D 471/08 (2013.01); C07D 471/10 (2013.01)

(58) Field of Classification Search
CPC .. C07D 413/14; C07D 417/04; C07D 417/14; C07D 413/04; A61K 31/5377; A61P 37/00
USPC ........................................ 544/135; 514/233.8
See application file for complete search history.

(56) References Cited

U.S. PATENT DOCUMENTS

| 4,088,768 | A | 5/1978 | Paget et al. |
| 2015/0105370 | A1 | 4/2015 | Carlson et al. |
| 2018/0037570 | A1 | 2/2018 | Sherer et al. |
| 2019/0185469 | A1 | 6/2019 | Dyckman et al. |
| 2021/0269451 | A1 | 2/2021 | Liu et al. |
| 2021/0340134 | A1 | 4/2021 | Qui et al. |
| 2021/0253575 | A1 | 8/2021 | Dey et al. |
| 2021/0300924 | A1 | 9/2021 | Liu et al. |
| 2021/0300947 | A1 | 9/2021 | Dey et al. |
| 2021/0323977 | A1 | 10/2021 | Liu et al. |
| 2021/0355122 | A1 | 11/2021 | Dey et al. |
| 2021/0395239 | A1 | 12/2021 | Dey et al. |
| 2022/0363665 | A1 | 11/2022 | Dey et al. |

FOREIGN PATENT DOCUMENTS

| CN | 103006645 A | 3/2013 |
| JP | 2009-542645 | 12/2009 |
| WO | 03/045385 A1 | 5/2003 |
| WO | 2015/057655 A1 | 4/2015 |
| WO | 2015/057659 A1 | 4/2015 |
| WO | 2017/106607 A1 | 6/2017 |
| WO | 2019/028302 A1 | 7/2017 |
| WO | 2018/031434 A1 | 2/2018 |
| WO | 2018/047081 A1 | 3/2018 |
| WO | 2018/049089 A1 | 3/2018 |
| WO | 2018/005586 A1 | 4/2018 |
| WO | 2018/026620 A1 | 8/2018 |
| WO | 2019/018354 A1 | 1/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |

(Continued)

OTHER PUBLICATIONS

Alper et al., "Discovery of potent, orally bioavailable in vivo efficacious antagonists of the TLR7/8 pathway" Bioorg. Med. Chem. Lett. 30(127366):1-5 ( 2020).
International Preliminary Report on Patentability for PCT/EP2018/073648 dated Mar. 9, 2021.
International Search Report for PCT/EP2018/073648 dated Nov. 27, 2018.
Knoepfel et al., "Target-Based Identification and Optimization of 5-Indazol-5-yl Pyridones as Toll-like Receptor 7 and 8 Antagonists Using a Biochemical TLR8 Antagonist Competition Assay" J. Med. Chem. 63:8276-8295 ( 2020).
Mussari et al., "Discovery of Potent and Orally Bioavailable Small Molecule Antagonists of Toll-like Receptors 7/8/9 (TLR7/8/9)" ACS Med. Chem. Lett. 11:1751-1758 ( 2020).

(Continued)

Primary Examiner — Charanjit Aulakh
(74) Attorney, Agent, or Firm — Genentech, Inc.; Richard G. A. Bone

(57) ABSTRACT

The present invention relates to compounds of formula (I), (I), wherein $R^1$, $R^2$ and $R^3$ are as described herein, and their pharmaceutically acceptable salt, enantiomer or diastereomer thereof, and compositions including the compounds and methods of using the compounds.

(I)

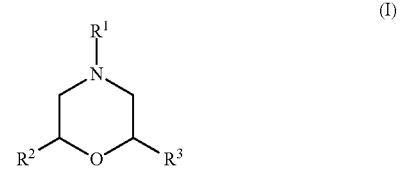

12 Claims, No Drawings

(56) References Cited

FOREIGN PATENT DOCUMENTS

| WO | 2019/126253 A1 | 6/2019 | |
|---|---|---|---|
| WO | 2019/028301 A1 | 7/2019 | |
| WO | 2019/220390 A1 | 11/2019 | |
| WO | 2019/238629 A1 | 12/2019 | |
| WO | WO 2019/238616 A1 * | 12/2019 | ........... C07D 413/14 |
| WO | 2020/043271 A1 | 3/2020 | |
| WO | 2020/048595 A1 | 3/2020 | |
| WO | 2020/048596 A1 | 3/2020 | |
| WO | 2020/048605 A1 | 3/2020 | |
| WO | 2020/064792 A1 | 4/2020 | |
| WO | 2020/094749 A1 | 5/2020 | |
| WO | 2021/048200 A1 | 3/2021 | |
| WO | 2021/099406 A1 | 5/2021 | |

OTHER PUBLICATIONS

Sabharwal et al., "Frentizole therapy in systemic Lupus Erythematosus" Arthritis and Rheumatism 23(12):1376-1380 (Dec. 1980).
USPTO et al., "U.S. Appl. No. 17/756,221 entitled Spiro(isobenzofuranazetidine) Compounds for the Treatment of Autoimmune Disease" (filed May 19, 2022).
"Written Opinion—PCT/EP2018/073648": pp. 1-5 (dated Nov. 27, 2018).

* cited by examiner

BENZOTHIAZOLE COMPOUNDS FOR THE TREATMENT OF AUTOIMMUNE DISEASES

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al Lancet 2011, 377, 721). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as auto-inflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7,8,9 is considered as a key node in a broad of autoimmune and auto-inflammatory diseases (Krieg, A. M. et al. Immunol. Rev. 2007, 220, 251. Jiménez-Dalmaroni, M. J. et al Autoimmun Rev. 2016, 15, 1. Chen, J. Q., et al. Clinical Reviews in Allergy & Immunology 2016, 50, 1.) Therefore, TLR7,8,9 represents a new therapeutic target for autoimmune and auto-inflammatory diseases, for which no effective steroid-free and non-cytotoxic oral drugs exist, and inhibition of these pathways from the very upstream may deliver satisfying therapeutic effects. From a safety perspective, because there are multiple nucleic acid sensing pathways (e.g. other TLRs, cGAS/STING), such redundancy should still allow responses to infection in the presence of TLR789 inhibition. As such, we proposed and invented oral compounds that target and suppress TLR7,8,9 for the treatment of autoimmune and auto-inflammatory diseases.

SUMMARY OF THE INVENTION

The present invention relates to novel compounds of formula (I),

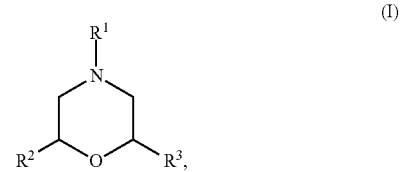

wherein
$R^1$ is

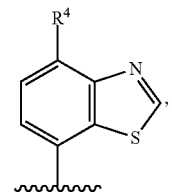

wherein $R^4$ is cyano, $C_{1-6}$alkyl, halogen, halo $C_{1-6}$alkyl or nitro;
$R^2$ is $C_{1-6}$alkyl, $C_{3-7}$cycloalkyl or halo $C_{1-6}$alkyl;
$R^3$ is —$C_{1-6}$alkyl-$R^5$ or —$CONR^6R^7$; wherein
  $R^5$ is heterocyclyl;
  $R^6$ is H;
  $R^7$ is heterocyclyl or heterocyclyl$C_{1-6}$alkylamino;
or a pharmaceutically acceptable salt, enantiomer or diastereomer thereof.

Another object of the present invention is related to novel compounds of formula (I), their manufacture, medicaments based on a compound in accordance with the invention and their production as well as the use of compounds of formula (I) as TLR7 and/or TLR8 and/or TLR9 antagonist, and for the treatment or prophylaxis of systemic lupus erythematosus or lupus nephritis. The compounds of formula (I) show superior TLR7 and/or TLR8 and/or TLR9 antagonism activity. In addition, the compounds of formula (I) also show good cytotoxicity, solubility, human microsome stability and SDPK profiles, as well as low CYP inhibition.

DETAILED DESCRIPTION OF THE INVENTION

Definitions

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "halogen" and "halo" are used interchangeably herein and denote fluoro, chloro, bromo, or iodo.

The term "halo$C_{1-6}$alkyl" denotes an alkyl group wherein at least one of the hydrogen atoms of the alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl, trifluoromethyl and trifluoroethyl.

The term "heterocyclyl" denotes a monovalent saturated or partly unsaturated mono- or bicyclic ring system of 3 to 12 ring atoms, comprising 1, 2, or 3 ring heteroatoms selected from N, O and S, the remaining ring atoms being carbon. In particular embodiments, heterocyclyl is a monovalent saturated monocyclic ring system of 4 to 10 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, oxazepanyl, diazepanyl, homopiperazinyl, or oxazepanyl. Examples for bicyclic saturated heterocyclyl are aminoazabicyclo[3.2.1]octanyl, aminoazabicyclo[3.2.1]octanyl, $C_{1-6}$alkyldiazaspiro[5.5]undecanyl, diazaspiro[3.5]nonanyl, diazaspiro[4.5]decanyl, diazaspiro[4.5]decanyl, diazaspiro[5.5]undecanyl and diazaspiro[5.5]undecanyl. Examples for partly unsaturated heterocyclyl are dihydrofuryl, imidazolinyl, dihydro-oxazolyl, tetrahydropyridinyl, and dihydropyranyl. Monocyclic or bicyclic heterocyclyl can be further substituted by halogen, hydroxy, amino, $C_{1-6}$alkyl, halo$C_{1-6}$alkyl or heterocyclyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to a compound of formula (I),

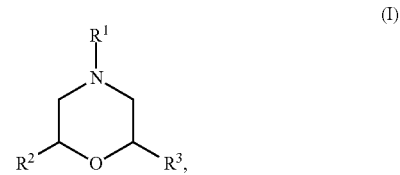

wherein
$R^1$ is

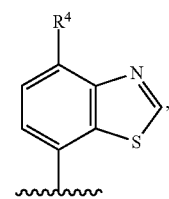

wherein $R^4$ is cyano, $C_{1-6}$alkyl, halogen, halo$C_{1-6}$alkyl or nitro;
$R^2$ is $C_{1-6}$alkyl, $C_{3-7}$cycloalkyl or halo$C_{1-6}$alkyl;
$R^3$ is —$C_{1-6}$alkyl-$R^5$ or —CONR$^6$R$^7$; wherein
  $R^5$ is heterocyclyl;
  $R^6$ is H;
  $R^7$ is heterocyclyl or heterocyclyl$C_{1-6}$alkylamino;
or a pharmaceutically acceptable salt, enantiomer or diastereomer thereof.

A further embodiment of present invention is (ii) a compound of formula (I), wherein
R¹ is

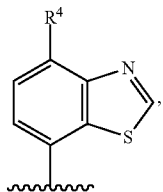

wherein R⁴ is cyano;
R² is $C_{1-6}$alkyl;
R³ is —$C_{1-6}$alkyl-R⁵ or —CONR⁶R⁷; wherein
R⁵ is aminoazabicyclo[3.2.1]octanyl, aminopiperidinyl, $C_{1-6}$alkyldiazaspiro[5.5]undecanyl, diazaspiro[3.5]nonanyl, diazaspiro[4.5]decanyl, diazaspiro[4.5]decanyl, diazaspiro[5.5]undecanyl, diazaspiro[5.5]undecanyl or piperidinylpiperidinyl;
R⁶ is H;
R⁷ is $C_{1-6}$alkylpiperidinyl or $C_{1-6}$alkylmorpholinyl$C_{1-6}$alkyl;
or a pharmaceutically acceptable salt, enantiomer or diastereomer thereof.

A further embodiment of present invention is (iii) a compound of formula (I) according to (ii), wherein R³ is —CH₂—R⁵ or —CONR⁶R⁷.

A further embodiment of present invention is (iv) a compound of formula (I) according to (iii), wherein R² is methyl.

A further embodiment of present invention is (v) a compound of formula (I) according to (iv), wherein R⁵ is 2,8-diazaspiro[3.5]nonan-2-yl, 2,8-diazaspiro[4.5]decan-8-yl, 2,9-diazaspiro[4.5]decan-2-yl, 2,9-diazaspiro[5.5]undecan-9-yl, 2-methyl-2,9-diazaspiro[5.5]undecan-9-yl, 3,9-diazaspiro[5.5]undecan-3-yl, 3-amino-8-azabicyclo[3.2.1]octan-8-yl, 4-(1-piperidinyl)-1-piperidinyl, 4-amino-1-piperidinyl.

A further embodiment of present invention is (vi) a compound of formula (I) according to (v), wherein R⁷ is 1-methyl-4-piperidinyl or 4-methylmorpholin-2-ylmethyl.

Another embodiment of present invention is that (vii) particular compounds of formula (I) are the following:
7-[(2S,6R)-2-(2,9-diazaspiro[4.5]decan-2-ylmethyl)-6-methyl-morpholin-4-yl]-1,3-benzothiazole-4-carbonitrile;
7-[(2S,6R)-2-[(4-amino-1-piperidyl)methyl]-6-methyl-morpholin-4-yl]-1,3-benzothiazole-4-carbonitrile;
7-[(2S,6R)-2-(2,9-diazaspiro[5.5]undecan-9-ylmethyl)-6-methyl-morpholin-4-yl]-1,3-benzothiazole-4-carbonitrile;
7-[(2S,6R)-2-(2,8-diazaspiro[3.5]nonan-2-ylmethyl)-6-methyl-morpholin-4-yl]-1,3-benzothiazole-4-carbonitrile;
7-[(2S,6R)-2-(3,9-diazaspiro[5.5]undecan-3-ylmethyl)-6-methyl-morpholin-4-yl]-1,3-benzothiazole-4-carbonitrile;
7-[(2S,6R)-2-(2,8-diazaspiro[4.5]decan-8-ylmethyl)-6-methyl-morpholin-4-yl]-1,3-benzothiazole-4-carbonitrile;
7-[(2R,6S)-2-methyl-6-[[4-(1-piperidyl)-1-piperidyl]methyl]morpholin-4-yl]-1,3-benzothiazole-4-carbonitrile;
Endo-7-[(2S,6R)-2-[[(1R,5S)-3-amino-8-azabicyclo[3.2.1]octan-8-yl]methyl]-6-methyl-morpholin-4-yl]-1,3-benzothiazole-4-carbonitrile;
Exo-7-[(2S,6R)-2-[[(1S,5R)-3-amino-8-azabicyclo[3.2.1]octan-8-yl]methyl]-6-methyl-morpholin-4-yl]-1,3-benzothiazole-4-carbonitrile;
7-[(2R,6S)-2-methyl-6-[(2-methyl-2,9-diazaspiro[5.5]undecan-9-yl)methyl]morpholin-4-yl]-1,3-benzothiazole-4-carbonitrile;
(2R,6R)-4-(4-cyano-1,3-benzothiazol-7-yl)-6-methyl-N-(1-methyl-4-piperidyl)morpholin-2-carboxamide;
(2R,6R)-4-(4-cyano-1,3-benzothiazol-7-yl)-6-methyl-N-[(4-methylmorpholin-2-yl)methyl]morpholine-2-carboxamide;
or a pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, R¹ to R⁷ are as defined above unless otherwise indicated. Furthermore, and unless explicitly otherwise stated, all reactions, reaction conditions, abbreviations and symbols have the meanings well known to a person of ordinary skill in organic chemistry.

A general synthetic route for preparing the compound of formula (I) is shown in Scheme 1 below.

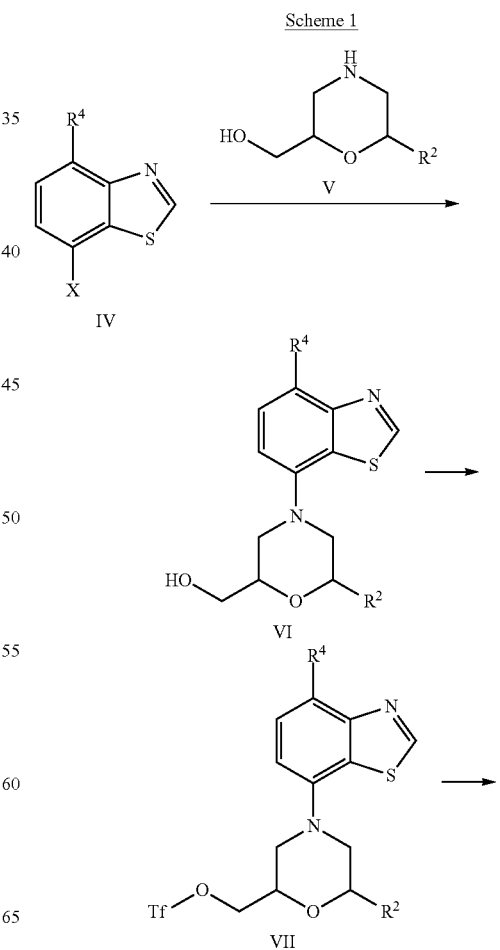

Scheme 1

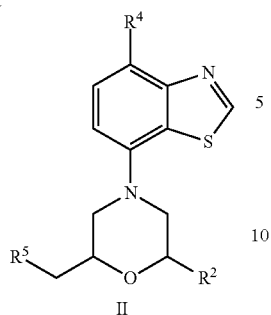

II wherein X is halogen.

The synthesis of the compound of formula (II) is shown in Scheme 1. The coupling of halide (IV) with compound of formula (V) can be achieved by direct coupling in the presence of a base, such as DIPEA or $K_2CO_3$, or under Buchwald-Hartwig amination conditions (ref: *Acc. Chem. Res.* 1998, 31, 805-818; *Chem. Rev.* 2016, 116, 12564-12649; *Topics in Current Chemistry*, 2002, 219, 131-209; and references cited therein) with a catalyst, such as Ruphos Pd-G2, and a base, such as $Cs_2CO_3$, to provide compound of formula (VI), which forms compound of formula (VII) in the presence of base, such as 2,6-dimethylpyridine, and a triflation reagent, such as $Tf_2O$. Substitution of compound of formula (VII) with amine in the presence of a base, such as $Cs_2CO_3$, gives the compound of formula (II). In some embodiment, the reaction of compound of formula (VII) with amine may give a product containing a protecting group, e.g. Boc, originated from amine, which will be removed before affording the final compound of formula (II).

A general synthetic route for preparing the compounds of formula (III) is shown in Scheme 2.

Scheme 2

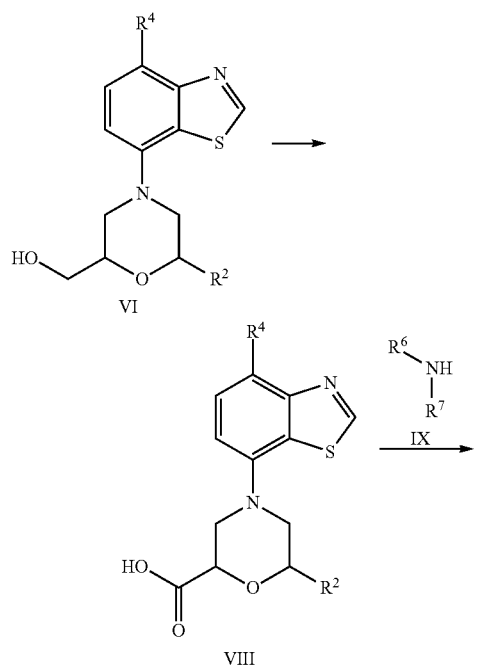

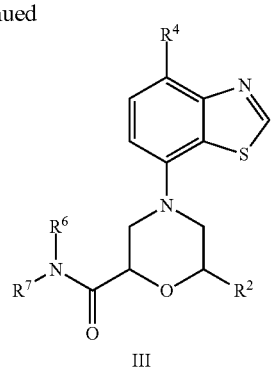

III wherein $R^6$ and $R^7$ are independently selected from H, heterocyclyl or heterocyclyl$C_{1-6}$alkylamino.

The alcohol (VI) can be oxidized by oxidation reagents, such as benzoyl peroxide/TEMPO, to afford compound of formula (VIII). Carboxylic acid (VIII) is applied to condensation conditions with amine (IX) in the presence of a coupling reagent, such as HATU, to give the compound of formula (III). In some embodiment, the reaction of compound of formula (VIII) and amine may give a product containing a protecting group, e.g. Boc, originated from amine (IX), which will be removed before affording the final compound of formula (III).

This invention also relates to a process for the preparation of a compound of formula (I) comprising any of the following steps:

a) substitution of compound of formula (VII),

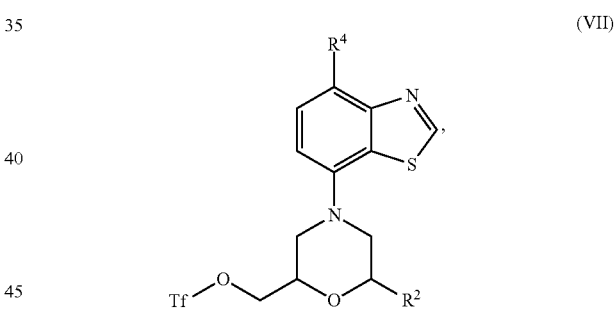

(VII)

with amine in the presence of a base;

b) the reaction of compound of formula (VIII),

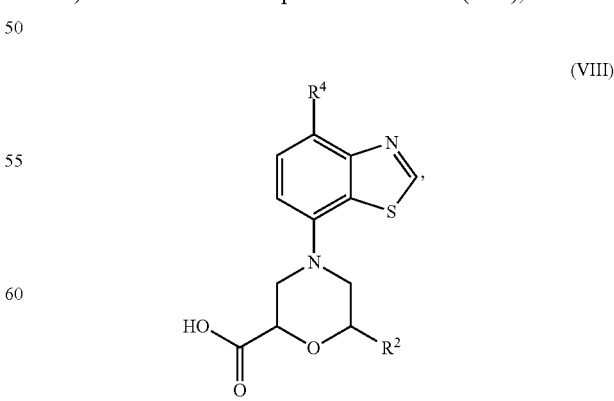

(VIII)

with amine (IX) in the presence of a coupling reagent; wherein $R^2$ and $R^4$ are defined above.

In step a), the base can be for example Cs$_2$CO$_3$.

In step b), the coupling reagent can be for example HATU.

A compound of formula (I), (II) or (III) when manufactured according to the above process is also an object of the invention.

Compounds of this invention can be obtained as mixtures of diastereomers or enantiomers, which can be separated by methods well known in the art, e.g. (chiral) HPLC or SFC.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:
ACN: acetonitrile
Boc$_2$O: di-tert-butyl dicarbonate
Tf$_2$O: triflic anhydride
DCM: dichloromethane
DDI drug-drug-interaction
DIPEA diethylisopropylamine
DMA dimethylacetamide
EA or EtOAc: ethyl acetate
FA: formic acid
HATU 1-[Bis(dimethylamino)methylene]-1H-1,2,3-triazolo[4,5-b]pyridinium 3-oxid hexafluorophosphate
HLM human liver microsome
hr hour
hrs hours
IC$_{50}$: half inhibition concentration
LCMS liquid chromatography-mass spectrometry
LYSA lyophilisation solubility assay
MS: mass spectrometry
PE: petroleum ether
prep-HPLC: preparative high performance liquid chromatography
rt: rt
RT: retention time
RuPhos Pd G2: chloro(2-dicyclohexylphosphino-2',6'-diisopropoxy-1,1'-biphenyl)[2-(2'-amino-1,1'-biphenyl)]palladium(II) 2nd generation
SFC: supercritical fluid chromatography
Tf: trifluoromethanesulfonyl
TFA: trifluoroacetic acid
v/v volume ratio General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBDTM 30×100 mm) column, SunFire™ Prep-C18 (5 μm, OBD™30×100 mm) column, Phenomenex Synergi-C18 (10 μm, 25×150 mm) or Phenomenex Gemini-C18 (10 μm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: CO$_2$ and IPA (0.5% TEA in IPA) or CO$_2$ and MeOH (0.1% NH$_3$.H$_2$O in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in H$_2$O; B: 0.1% TFA in acetonitrile;

Acidic condition II: A: 0.0375% TFA in H$_2$O; B: 0.01875% TFA in acetonitrile;

Basic condition I: A: 0.1% NH$_3$.H$_2$O in H$_2$O; B: acetonitrile;

Basic condition II: A: 0.025% NH$_3$.H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (MH)$^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

PREPARATIVE EXAMPLES

The following examples are intended to illustrate the meaning of the present invention but should by no means represent a limitation within the meaning of the present invention:

Example 1

7-[(2S,6R)-2-(2,9-diazaspiro[4.5]decan-2-ylmethyl)-6-methyl-morpholin-4-yl]-1,3-benzothiazole-4-carbonitrile

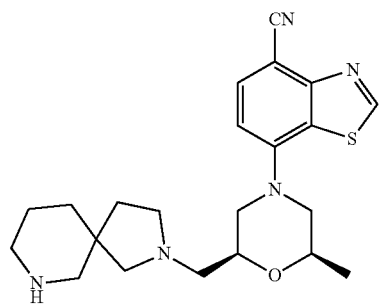 [SMILES: C[C@@H]1CN(c2ccc(C#N)c3ncsc23)C[C@H](CN2CCC3(CCCNC3)C2)O1]

The title compound was prepared according to the following scheme:

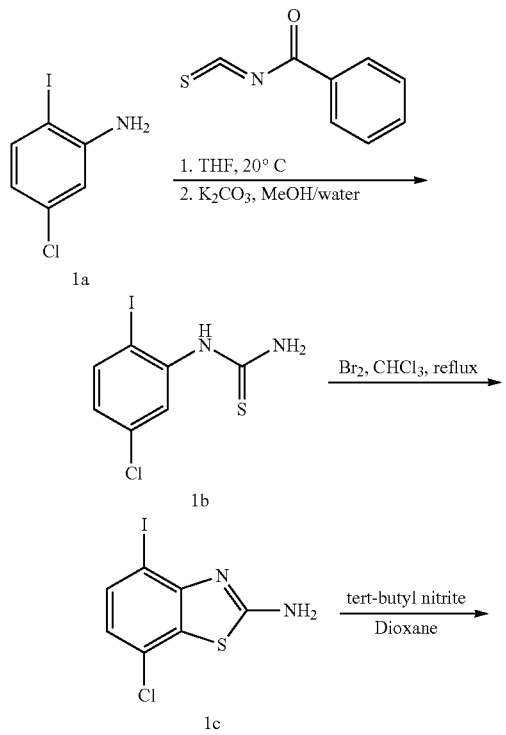

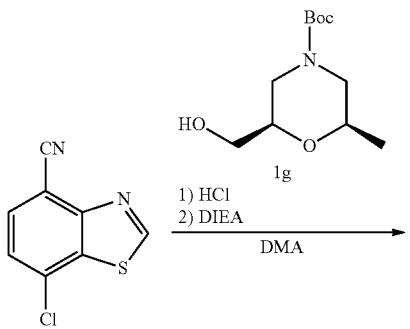

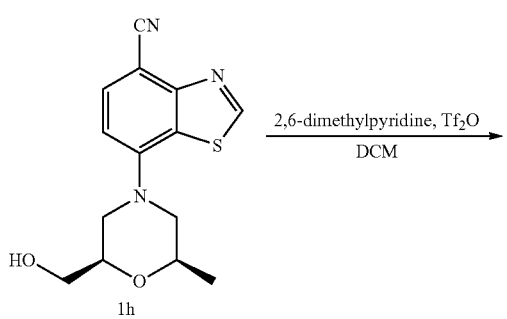

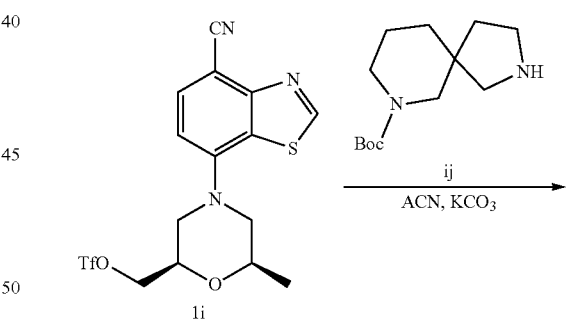

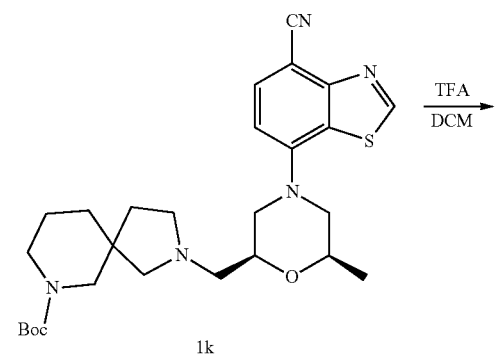

-continued

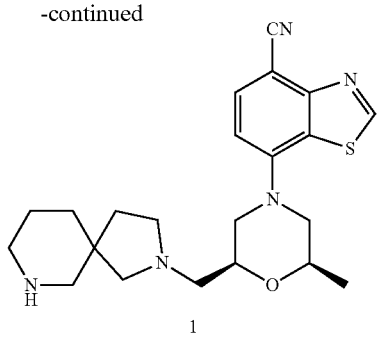

1

Step 1: preparation of 1-(5-chloro-2-iodophenyl)thiourea (compound 1b)

To a solution of 5-chloro-2-iodo-aniline (compound 1a, 5.0 g, 19.7 mmol) in THF (87 mL) was added benzoyl isothiocyanate (CAS: 532-55-8, 6.4 g, 39.4 mmol) at 10-20° C. After the reaction was stirred at 20° C. for 16 hrs, the solvent was removed under vaccum and the solid was washed with a mixed solvent of EtOH (40 mL) and PE (10 mL), followed by air-drying to afford 8.7 g of intermediate. The intermediate was dissolved in methanol (100 mL) and treated with a solution of potassium carbonate (8.2 g, 59.2 mmol) in water (40 mL). The reaction mixture was heated at 70° C. for 4 hrs, then the solvent was removed under vaccum followed by addition of water (20 mL). The solid was collected by filtration, further washed with water (20 mL), and dried to afford compound 1b (5.0 g, 16.0 mmol, 81% yield) as a yellow solid.

Step 2: preparation of 7-chloro-4-iodo-1,3-benzothiazol-2-amine (compound 1c)

To a solution of 1-(5-chloro-2-iodophenyl)thiourea (compound 1b, 4.0 g, 12.8 mmol) in chloroform (32 mL) was added bromine (0.66 mL, 12.8 mmol). The reaction mixture was heated at 78° C. for 18 hrs. After the reaction was cooled to rt, the solvent was removed under vaccum and the solid was dissolved into a mixed solvent of DCM: MeOH (100 mL, 1:1), to which aqueous solution of $Na_2S_2O_3$ (sat., 20 mL) was added. Then the solvent was removed under vaccum, and 30 mL of water was added. The solid was collected by filtration, and dried to give the desired product compound 1c (3.5 g, 11.3 mmol, 88% yield) as a yellow solid. MS calc'd 311 [(M+H)$^+$]; measured 311 [(M+H)$^+$].

Step 3: preparation of 7-chloro-4-iodo-1,3-benzothiazole (compound 1d)

To a solution of 7-chloro-4-iodo-1,3-benzothiazol-2-amine (compound 1c, 3.0 g, 9.7 mmol) in 1,4-dioxane (60 mL) was added tert-butyl nitrite (2.0 g, 19.3 mmol). The reaction mixture was heated at 90° C. for 18 hrs and then the solvent was removed under vaccum. The residue was purified by silica-gel column chromatography (PE) to give the crude product, which was triturated in PE (15 mL) to give the desired product compound 1d (1.5 g, 5.1 mmol, 52% yield) as a white solid. MS calc'd 296 [(M+H)$^+$]; measured 296 [(M+H)$^+$].

Step 4: preparation of 7-chloro-1,3-benzothiazole-4-carbonitrile (compound 1f)

To a solution of 7-chloro-4-iodo-1,3-benzothiazole (compound 1d, 1.5 g, 5.1 mmol) in DMA (40 mL) was added zinc cyanide (0.89 g, 7.6 mmol) and tetrakis(triphenylphosphine) palladium(0) (0.2 g, 0.17 mmol). The reaction mixture was heated at 100° C. for 18 hrs and then poured into water (100 mL). The solid was collected by filtration, and dissolved in EA (400 mL). The organic layer was washed with brine, dried over anhydrous $Na_2SO_4$ and concentrated to give the desired product compound 1f (0.9 g, 4.6 mmol, 91% yield) as a white solid. MS calc'd 195 [(M+H)$^+$]; measured 195 [(M+H)$^+$].

Step 5: preparation of 7-[(2R,6R)-2-(hydroxymethyl)-6-methyl-morpholin-4-yl]-1,3-benzothiazole-4-carbonitrile (compound 1h)

To a solution of [(2R,6R)-6-methylmorpholin-2-yl]methanol (compound 1g, WuXi Apptec, CAS: 1700609-48-8, 60.6 mg, 0.26 mmol) in DCM (2 mL) was added HCl (0.5 mL, 10% in MeOH) at rt. After the reaction mixture was stirred at rt for 2 hrs, the solvent was removed under vaccum and the residue was dissolved in DMA (0.5 mL). To the solution was added 7-chloro-1,3-benzothiazole-4-carbonitrile (compound 1f, 51.7 mg, 0.31 mmol) and N,N-diisopropylethylamine (0.13 mL, 0.77 mmol). After the reaction mixture was stirred at 150° C. for 2 hrs, water (10 mL) was added. Then the mixture was cooled and extracted with EA (10 mL). The organic layer was washed with brine, dried over anhydrous $Na_2SO_4$, and concentrated to give the residue, which was purified by prep-TLC (PE:EA=2:1) to give the desired product compound 1h (15 mg, 0.050 mmol, 20% yield) as a yellow gum. MS calc'd 290 [(M+H)$^+$]; measured 290 [(M+H)$^+$].

Step 6: preparation of ((2R,6R)-4-(4-cyano-1,3-benzothiazol-7-yl)-6-methylmorpholin-2-yl)methyl trifluoromethanesulfonate (compound 1i)

To a solution of 7-[(2R,6R)-2-(hydroxymethyl)-6-methyl-morpholin-4-yl]-1,3-benzothiazole-4-carbonitrile (compound 1h, 15.0 mg, 0.050 mmol) in DCM (1 mL) was added 2,6-dimethylpyridine (22.2 mg, 0.21 mmol) and trifluoromethanesulfonic anhydride (29.2 mg, 0.10 mmol). The reaction mixture was stirred at 0° C. for 1 hr and then poured into ice-water (10 mL). The mixture was extracted with DCM (10 mL). The organic layer was dried over $Na_2SO_4$, and concentrated to give compound 1i (20 mg, 0.050 mmol, 91% yield) as a yellow solid.

Step 7: preparation of tert-butyl 2-(((2S,6R)-4-(4-cyano-1,3-benzothiazol-7-yl)-6-methylmorpholin-2-yl)methyl)-2,7-diazaspiro[4.5]decane-7-carboxylate (compound 1k).

To a solution of ((2R,6R)-4-(4-cyano-1,3-benzothiazol-7-yl)-6-methylmorpholin-2-yl)methyl trifluoromethanesulfonate (compound 1i, 20.0 mg, 0.050 mmol) in ACN (2 mL) was added compound 1j (PharmaBlock, CAS: 236406-61-4, 14.83 mg, 0.060 mmol) and potassium carbonate (13.12 mg, 0.090 mmol). After the reaction mixture was stirred at 60° C. for 14 hrs, EtOAc (20 mL) was added. Then the mixture was filtered and concentrated to afford compound 1k (30 mg, 0.060 mmol, ca. 100%, crude yield) as a yellow solid. MS calc'd 512 [(M+H)$^+$]; measured 512 [(M+H)$^+$].

Step 8: preparation of 7-[rac-(2S,6R)-2-(2,9-diazaspiro[4.5]decan-2-ylmethyl)-6-methyl-morpholin-4-yl]-1,3-benzothiazole-4-carbonitrile (Example 1)

To a solution of tert-butyl 2-(((2S,6R)-4-(4-cyano-1,3-benzothiazol-7-yl)-6-methylmorpholin-2-yl)methyl)-2,7-diazaspiro[4.5]decane-7-carboxylate (compound 1k, 20.0 mg, 0.040 mmol) in DCM (1 mL) was added trifluoroacetic acid (0.1 mL). The reaction mixture was stirred at 20° C. for 1 hr, then the solvent was removed. The residue was purified by prep-HPLC (HCl) to give the desired product Example 1 (2.4 mg, 0.010 mmol, 15% yield) as yellow gum. MS calc'd 412 [(M+H)$^+$]; measured 412 [(M+H)$^+$]. $^1$H NMR (400 MHz, METHANOL-d$_4$) δ ppm: 9.43 (s, 1H), 7.92 (d, J=8.0 Hz, 1H), 7.19 (d, J=8.0 Hz, 1H), 4.31 (s, 1H), 4.06 (s, 1H), 3.97-3.86 (m, 2H), 3.81-3.66 (m, 3H), 3.63-3.34 (m, 5H), 3.26-3.12 (m, 2H), 2.88-2.72 (m, 2H), 2.40-2.08 (m, 2H), 1.91 (s, 4H), 1.36 (d, J=5.8 Hz, 3H).

Example 2

7-[(2S,6R)-2-[(4-amino-1-piperidyl)methyl]-6-methyl-morpholin-4-yl]-1,3-benzothiazole-4-carbonitrile

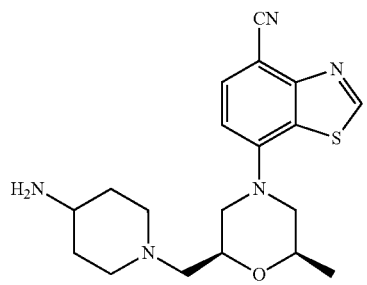 [SMILES: C[C@@H]1CN(c2ccc(C#N)c3ncsc23)C[C@H](CN2CCC(N)CC2)O1]

The title compound was prepared in analogy to the preparation of Example 1 by using 4-Boc-aminopiperidine (PharmaBlock, CAS: 73874-95-0) instead of tert-butyl 2,7-diazaspiro[4.5]decane-7-carboxylate (compound 1j). Example 2 (1.2 mg) was obtained as white gum. MS calc'd 372 [(M+H)+]; measured 372 [(M+H)+]. $^1$H NMR (400 MHz, METHANOL-$d_4$) δ ppm: 9.43 (s, 1H), 7.93 (d, J=8.3 Hz, 1H), 7.18 (d, J=8.4 Hz, 1H), 4.40-4.34 (m, 1H), 4.11-4.03 (m, 1H), 3.96-3.66 (m, 5H), 3.57-3.47 (m, 1H), 3.46-3.39 (m, 2H), 3.31-3.23 (m, 1H), 2.90-2.71 (m, 2H), 2.38-2.28 (m, 2H), 2.22-2.08 (m, 2H), 1.35 (d, J=6.3 Hz, 3H).

Example 3

7-[(2S,6R)-2-(2,9-diazaspiro[5.5]undecan-9-ylmethyl)-6-methyl-morpholin-4-yl]-1,3-benzothiazole-4-carbonitrile

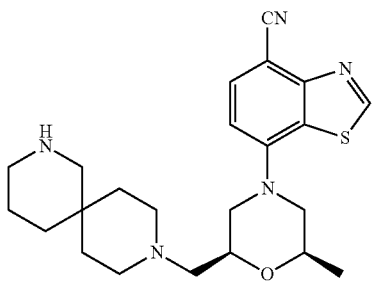 [SMILES: C[C@@H]1CN(c2ccc(C#N)c3ncsc23)C[C@H](CN2CCC3(CCCNC3)CC2)O1]

The title compound was prepared in analogy to the preparation of Example 1 by using tert-butyl 2,9-diazaspiro[5.5]undecane-9-carboxylate (PharmaBlock, CAS: 189333-03-7) instead of tert-butyl 2,7-diazaspiro[4.5]decane-7-carboxylate (compound 1j). Example 3 (7.2 mg) was obtained as yellow gum. MS calc'd 425 [(M+H)+]; measured 426 [(M+H)+]. $^1$H NMR (400 MHz, METHANOL-$d_4$) δ ppm: 9.43 (s, 1H), 7.93 (d, J=8.2 Hz, 1H), 7.18 (d, J=8.3 Hz, 1H), 4.40-4.31 (m, 1H), 4.09-4.01 (m, 1H), 3.77-3.59 (m, 4H), 3.52-3.39 (m, 2H), 3.32-3.26 (m, 2H), 3.21-3.15 (m, 2H), 3.06 (s, 1H), 2.89-2.73 (m, 2H), 2.16-2.01 (m, 2H), 1.89 (s, 6H), 1.69-1.65 (m, 1H), 1.35 (d, J=6.3 Hz, 3H).

Example 4

7-[(2S,6R)-2-(2,8-diazaspiro[3.5]nonan-2-ylmethyl)-6-methyl-morpholin-4-yl]-1,3-benzothiazole-4-carbonitrile

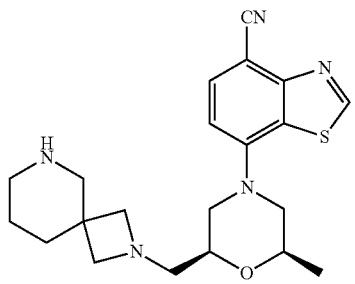 [SMILES: C[C@@H]1CN(c2ccc(C#N)c3ncsc23)C[C@H](CN2CC3(CCCNC3)C2)O1]

The title compound was prepared in analogy to the preparation of Example 1 by using tert-butyl 2,6-diazaspiro[3.5]nonane-6-carboxylate (WuXi Apptec, CAS: 885272-17-3) instead of tert-butyl 2,7-diazaspiro[4.5]decane-7-carboxylate (compound 1j). Example 4 (9.7 mg) was obtained as white gum. MS calc'd 398 [(M+H)+]; measured 398 [(M+H)+]. $^1$H NMR (400 MHz, METHANOL-$d_4$) δ ppm: 9.40 (s, 1H), 7.89 (d, J=8.1 Hz, 1H), 7.12 (d, J=8.1 Hz, 1H), 4.04-3.63 (m, 8H), 3.39 (s, 2H), 3.11 (d, J=4.1 Hz, 4H), 2.87-2.63 (m, 2H), 2.00 (s, 2H), 1.82 (s, 2H), 1.29 (d, J=5.8 Hz, 3H).

Example 5

7-[(2S,6R)-2-(3,9-diazaspiro[5.5]undecan-3-ylmethyl)-6-methyl-morpholin-4-yl]-1,3-benzothiazole-4-carbonitrile

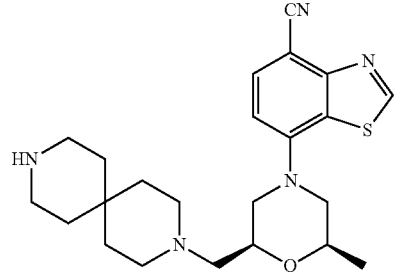 [SMILES: C[C@@H]1CN(c2ccc(C#N)c3ncsc23)C[C@H](CN2CCC3(CCNCC3)CC2)O1]

The title compound was prepared in analogy to the preparation of Example 1 by using tert-butyl 3,9-diazaspiro[5.5]undecane-3-carboxylate (Bide, CAS: 173405-78-2) instead of tert-butyl 2,7-diazaspiro[4.5]decane-7-carboxylate (compound 1j). Example 5 (7.0 mg) was obtained as yellow gum. MS calc'd 426 [(M+H)+]; measured 426 [(M+H)+]. $^1$H NMR (400 MHz, METHANOL-$d_4$) δ ppm: 9.43 (s, 1H), 7.93 (d, J=8.3 Hz, 1H), 7.18 (d, J=8.2 Hz, 1H), 4.35 (t, J=10.0 Hz, 1H), 4.09-4.02 (m, 1H), 3.78-3.56 (m, 4H), 3.51-3.36 (m, 2H), 3.30-3.23 (m, 6H), 2.87-2.73 (m, 2H), 2.11-1.95 (m, 4H), 1.91-1.73 (m, 4H), 1.34 (d, J=6.1 Hz, 3H).

Example 6

7-[(2S,6R)-2-(2,8-diazaspiro[4.5]decan-8-ylmethyl)-6-methyl-morpholin-4-yl]-1,3-benzothiazole-4-carbonitrile

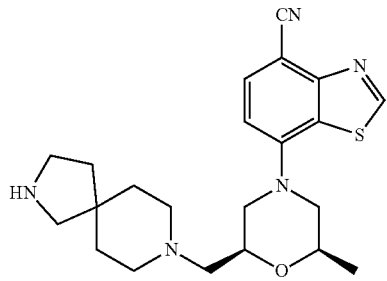 [SMILES: C[C@@H]1CN(c2ccc(C#N)c3ncsc23)C[C@H](CN2CCC3(CCNC3)CC2)O1]

The title compound was prepared in analogy to the preparation of Example 1 by using tert-butyl 2,8-diazaspiro[4.5]decane-2-carboxylate (PharmaBlock, CAS: 336191-17-4) instead of tert-butyl 2,7-diazaspiro[4.5]decane-7-carboxylate (compound 1j). Example 6 (11.1 mg) was obtained as a yellow solid. MS calc'd 412 [(M+H)$^+$]; measured 412 [(M+H)$^+$]. $^1$H NMR (400 MHz, METHANOL-d$_4$) δ ppm: 9.41 (s, 1H), 7.90 (d, J=8.2 Hz, 1H), 7.14 (d, J=8.3 Hz, 1H), 4.24-4.15 (m, 1H), 4.03-3.93 (m, 1H), 3.77-3.68 (m, 2H), 3.43 (t, J=7.4 Hz, 2H), 3.19 (s, 2H), 3.14-2.96 (m, 6H), 2.83-2.68 (m, 2H), 2.02 (t, J=7.4 Hz, 2H), 1.88 (t, J=5.3 Hz, 4H), 1.31 (d, J=6.1 Hz, 3H).

Example 7

7-[(2R,6S)-2-methyl-6-[[4-(1-piperidyl)-1-piperidyl]methyl]morpholin-4-yl]-1,3-benzothiazole-4-carbonitrile

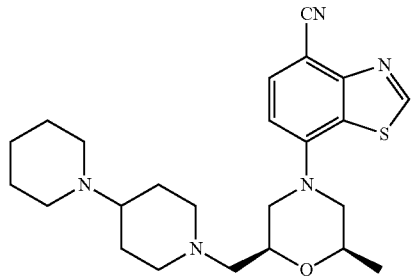 [SMILES: C[C@@H]1CN(c2ccc(C#N)c3ncsc23)C[C@H](CN2CCC(N3CCCCC3)CC2)O1]

The title compound was prepared in analogy to the preparation of Example 1 by using 4-piperidinopiperidine (Titan, CAS: 4897-50-1) instead of tert-butyl 2,7-diazaspiro[4.5]decane-7-carboxylate (compound 1j). Example 7 (11.79 mg) was obtained as a white solid. MS calc'd 440 [(M+H)$^+$]; measured 440 [(M+H)$^+$]. $^1$H NMR (400 MHz, METHANOL-d$_4$) δ ppm: 9.41 (s, 1H), 7.88 (d, J=8.0 Hz, 1H), 7.15 (d, J=8.2 Hz, 1H), 4.41 (t, J=8.8 Hz, 1H), 4.13-3.82 (m, 3H), 3.81-3.53 (m, 6H), 3.52-3.34 (m, 3H), 3.11 (t, J=10.9 Hz, 2H), 2.91-2.71 (m, 2H), 2.54-2.22 (m, 4H), 2.06-1.84 (m, 5H), 1.51-1.64 (m, 1H), 1.34 (d, J=6.0 Hz, 3H).

Example 8

Endo-7-[(2S,6R)-2-[[(1R,5S)-3-amino-8-azabicyclo[3.2.1]octan-8-yl]methyl]-6-methyl-morpholin-4-yl]-1,3-benzothiazole-4-carbonitrile

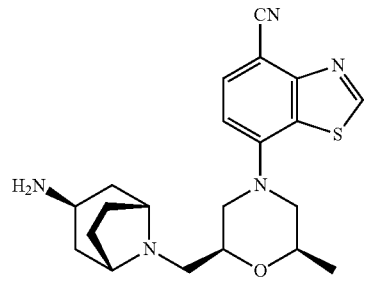

The title compound was prepared in analogy to the preparation of Example 1 by using tert-butyl N-[endo-8-azabicyclo[3.2.1]octan-3-yl]carbamate (PharmaBlock, CAS: 132234-69-6) instead of tert-butyl 2,7-diazaspiro[4.5]decane-7-carboxylate (compound 1j). Example 8 (8.3 mg) was obtained as a yellow solid. MS calc'd 398 [(M+H)$^+$]; measured 398 [(M+H)$^+$]. $^1$H NMR (400 MHz, METHANOL-d4) δ ppm: 9.40 (s, 1H), 7.89 (d, J=8.3 Hz, 1H), 7.13 (d, J=8.3 Hz, 1H), 4.11-4.01 (m, 1H), 4.00-3.91 (m, 1H), 3.88 (d, J=12.0 Hz, 1H), 3.77 (s, 1H), 3.69 (d, J=12.0 Hz, 1H), 3.62 (s, 1H), 3.55-3.52 (m, 1H), 2.92-2.84 (m, 1H), 2.81-2.70 (m, 3H), 2.59-2.51 (m, 2H), 2.37-2.20 (m, 2H), 1.98-1.88 (m, 2H), 1.74 (t, J=12.1 Hz, 2H), 1.29 (d, J=6.3 Hz, 3H).

Example 9

Exo-7-[(2S,6R)-2-[[(1S,5R)-3-amino-8-azabicyclo[3.2.1]octan-8-yl]methyl]-6-methyl-morpholin-4-yl]-1,3-benzothiazole-4-carbonitrile

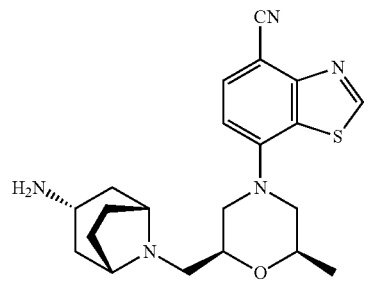

The title compound was prepared in analogy to the preparation of Example 1 by using tert-butyl N-[exo-8-azabicyclo[3.2.1]octan-3-yl]carbamate (WuXi Apptec, CAS: 132234-68-5) instead of tert-butyl 2,7-diazaspiro[4.5]decane-7-carboxylate (compound 1j). Example 9 (21.2 mg) was obtained as a white solid. MS calc'd 398 [(M+H)$^+$]; measured 398 [(M+H)$^+$]. $^1$H NMR (400 MHz, METHANOL-d$_4$) δ ppm: 9.39 (s, 1H), 7.89 (d, J=8.4 Hz, 1H), 7.13 (d, J=8.4 Hz, 1H), 4.15-4.07 (m, 1H), 3.96-3.90 (m, 1H), 3.87-3.79 (m, 2H), 3.73-3.65 (m, 2H), 3.55-3.45 (m, 1H), 2.95-2.90 (m, 1H), 3.85-3.70 (m, 3H), 2.25-2.13 (m, 2H), 1.99-1.92 (m, 4H), 1.86-1.75 (m, 2H), 1.28 (d, J=6.0 Hz, 3H).
Example 10
7-[(2R,6S)-2-methyl-6-[(2-methyl-2,9-diazaspiro[5.5]undecan-9-yl)methyl]morpholin-4-yl]-1,3-benzothiazole-4-carbonitrile
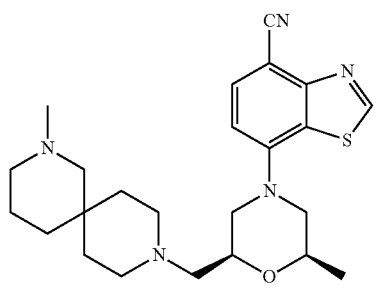 [SMILES: C[C@@H]1CN(c2ccc(C#N)c3ncsc23)C[C@H](CN2CCC3(CCCN(C)C3)CC2)O1]
The title compound was prepared according to the following scheme:
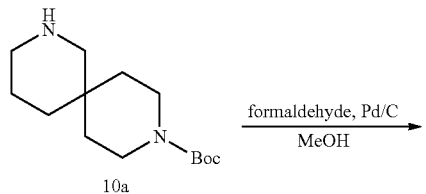
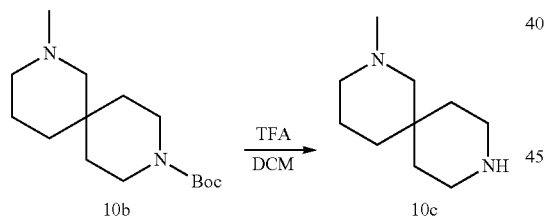
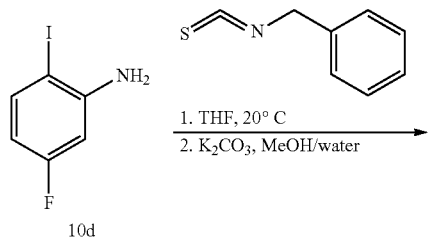
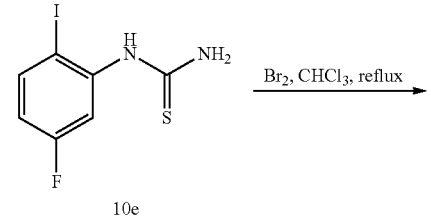
-continued
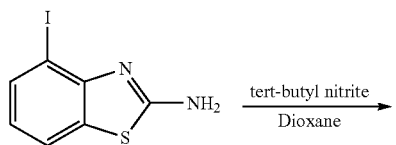
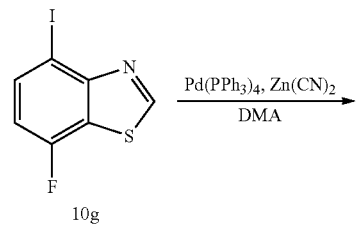
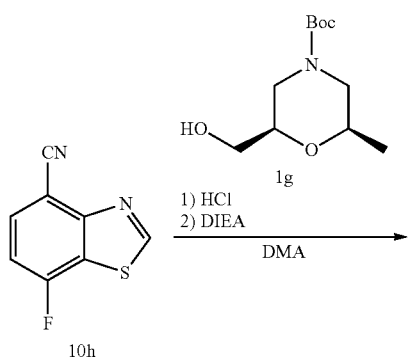
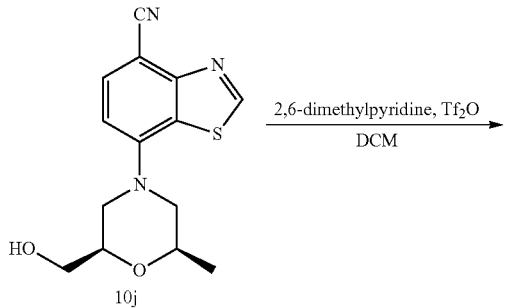
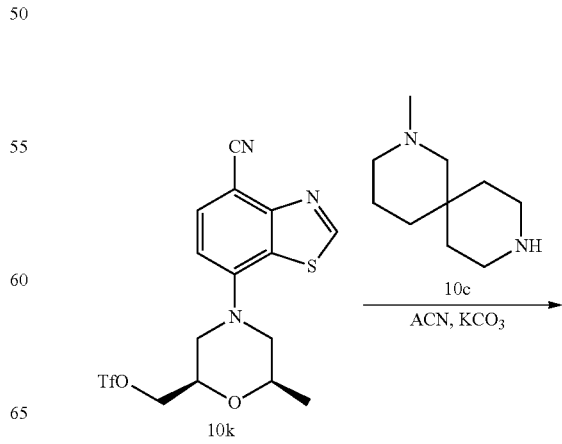

-continued

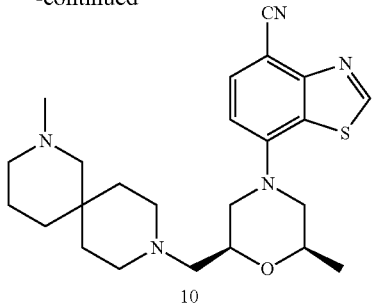

10

Step 1: Preparation of tert-butyl 2-methyl-2,9-diazaspiro[5.5]undecane-9-carboxylate (Compound 10b)

To a solution of tert-butyl 2,9-diazaspiro[5.5]undecane-9-carboxylate (compound 10a, PharmaB lock, CAS: 1023595-19-8, 0.15 g, 0.59 mmol) in methanol (6 mL) was added formaldehyde (0.4 g, 4.9 mmol, 37%) and Pd/C (20.0 mg, 10%). The reaction mixture was stirred under $H_2$ (1 atm) at 25° C. for 18 hrs. The mixture was filtered and the filtrate was concentrated under vaccum to afford compound 10b (0.15 g, 0.56 mmol, 95% yield) as a colorless gum.

Step 2: Preparation of 2-methyl-2,9-diazaspiro[5.5]undecane (Compound 10c)

To a solution of tert-butyl 2-methyl-2,9-diazaspiro[5.5]undecane-9-carboxylate (compound 10b, 0.15 g, 0.56 mmol) in DCM (2 mL) was added trifluoroacetic acid (0.68 mL, 8.8 mmol). After the reaction mixture was stirred at 20° C. for 1 hr, the solvent was removed under vaccum and the residue was re-dissolved in ACN/DCM (10 mL, 1:1). The resultant solution was basified to pH=8 with solid $NaHCO_3$, and the precipitant was filtered off. The filtrate was concentrated under vaccum to afford the desired product compound 10c (100 mg, 0.59 mmol, ca. 100% crude yield) as yellow oil, which was used in the next step without purification.

Step 3: Preparation of (5-fluoro-2-iodo-phenyl)thiourea (Compound 10e)

To a solution of 5-fluoro-2-iodo-aniline (compound 10d, 20.0 g, 84.4 mmol) in THF (375 mL) was added benzoyl isothiocyanate (CAS: 532-55-8, 27.0 g, 168.8 mmol) at 10-20° C. After the reaction mixture was stirred at 20° C. for 16 hrs, the solvent was removed under vaccum, followed by addition of EtOH (80 mL). The precipitate was collected by filtration and air-dried to afford an intermediate (34.0 g). The intermediate was re-dissolved into methanol (430 mL) and a solution of potassium carbonate (35.0 g) in water (50 mL) was added. After the reaction mixture was stirred at 70° C. for 4 hrs and then cooled to rt, the solvent was removed under vaccum, and the residue was purified by silica-gel column chromatography to afford the desired product compound 10e (19.0 g, 64.2 mmol, 76% yield) as a white solid. MS calc'd 297 [(M+H)$^+$]; measured 297 [(M+H)$^+$].

Step 4: Preparation of 7-fluoro-4-iodo-1,3-benzothiazol-2-amine (Compound 10f)

To a solution of (5-fluoro-2-iodo-phenyl)thiourea (compound 10e, 20.0 g, 67.5 mmol) in chloroform (360 mL) was added bromine (3.5 mL, 67.5 mmol) at 10° C. After the reaction mixture was stirred at 80° C. for 4 hrs and then diluted with MeOH (50 mL) at rt, $Na_2S_2O_3$ (sat., 100 mL) and $NaHCO_3$ (sat., 100 mL) was added. The organic layer was separated, washed with brine (100 mL), dried over anhydrous $Na_2SO_4$ and concentrated. The crude product was purified by silica-gel column chromatography (PE:EA=10:1) to afford the desired product compound 10f (6.7 g, 22.8 mmol, 33% yield) as a white solid. MS calc'd 295 [(M+H)$^+$]; measured 295 [(M+H)$^+$].

Step 5: Preparation of 7-fluoro-4-iodo-1,3-benzothiazole (Compound 10g)

To a solution of 7-fluoro-4-iodo-1,3-benzothiazol-2-amine (compound 10f, 4.0 g, 13.6 mmol) in 1,4-dioxane (84 mL) was added tert-butyl nitrite (2.8 g, 27.2 mmol). After the reaction mixture was heated at 80° C. for 18 hrs, the solvent was removed under vaccum. The residue was purified by silica-gel column chromatograph (PE:EA=10:1) to afford the desired product compound 10g (3.5 g, 12.5 mmol, 92% yield) as a yellow solid. MS calc'd 280 [(M+H)$^+$]; measured 280 [(M+H)$^+$].

Step 6: Preparation of 7-fluoro-1,3-benzothiazole-4-carbonitrile (Compound 10h)

To a solution of 7-fluoro-4-iodo-1,3-benzothiazole (compound 10g, 4.4 g, 15.8 mmol) in DMA (156 mL) was added zinc cyanide (2.7 g, 23.6 mmol), and tetrakis(triphenylphosphine)palladium(0) (0.66 g, 0.57 mmol). After the reaction mixture was stirred at 100° C. for 18 hrs and then cooled to rt, water (100 mL) was added, and the resultant mixture was extracted with EA (100 mL). The organic layers were combined, washed with brine (20 mL), dried over anhydrous $Na_2SO_4$, filtered, and concentrated. The residue was purified by silica-gel column chromatography (PE:EA=20:1-10:1) to give the desired product compound 10h (2.3 g, 12.9 mmol, 81% yield) as a white solid. MS calc'd 179 [(M+H)$^+$]; measured 179 [(M+H)$^+$].

Step 7: Preparation of 7-[(2R,6R)-2-(hydroxymethyl)-6-methyl-morpholin-4-yl]-1,3-benzothiazole-4-carbonitrile (Compound 10j)

To a solution of [(2R,6R)-6-methylmorpholin-2-yl]methanol (compound 1g, WuXi Apptec, CAS: 1700609-48-8, 311.8 mg, 1.3 mmol) in THF (20 mL) was added HCl (5 mL, 10% in MeOH) at rt. After the reaction mixture was stirred at rt for 2 hrs, the solvent was removed under vaccum and the residue was dissolved in DMA (3 mL). To the resultant solution was added 7-fluoro-1,3-benzothiazole-4-carbonitrile (compound 10h, 0.2 g, 1.1 mmol) and N,N-diisopropylethylamine (0.6 mL, 3.4 mmol). After the reaction was stirred at 130° C. for 18 hrs then cooled to rt, water (15 mL) was added, and the resultant mixture was extracted with EA (2×10 mL). The organic layers were washed with brine, dried over anhydrous $Na_2SO_4$ and concentrated. The residue was purified by silica-gel column chromatography (PE:EA=5:1) to afford the desired product compound 10j (0.3 g, 1.0 mmol, 92% yield) as a yellow solid. MS calc'd 290 [(M+H)$^+$]; measured 290 [(M+H)$^+$].

Step 8: Preparation of ((2R,6R)-4-(4-cyano-1,3-benzothiazol-7-yl)-6-methylmorpholin-2-yl)methyl trifluoromethanesulfonate (Compound 10k)

To the solution of 7-[(2R,6R)-2-(hydroxymethyl)-6-methyl-morpholin-4-yl]-1,3-benzothiazole-4-carbonitrile (compound 10j, 25.0 mg, 0.090 mmol) in DCM (1.3 mL) was added 2,6-dimethylpyridine (37.0 mg, 0.35 mmol) and trifluoromethanesulfonic anhydride (48.7 mg, 0.17 mmol). After the mixture was stirred at 0° C. for 1 hr, it was added to ice-water (10 mL) and extracted with DCM (10 mL). The organic layer was dried over $Na_2SO_4$, filtered and concentrated to afford compound 10k (36.0 mg, 0.090 mmol, 98% yield) as yellow gum, which was used for the next step without purification.

Step 7: Preparation of 7-[(2R,6S)-2-methyl-6-[(2-methyl-2,9-diazaspiro[5.5]undecan-9-yl)methyl]morpholin-4-yl]-1,3-benzothiazole-4-carbonitrile (Example 10)

To the solution of [(2R,6R)-4-(cyano-1,3-benzothiazol-7-yl)-6-methyl-morpholin-2-yl]methyl trifluoromethanesulfonate (compound 10k, 36.0 mg, 0.090 mmol) in ACN (2.2 mL) was added 2-methyl-2,9-diazaspiro[5.5]undecane (compound 10c, 18.7 mg, 0.11 mmol) and potassium carbonate (23.6 mg, 0.17 mmol). After the reaction mixture was stirred at 55° C. for 4 hrs then cooled to rt, EtOAc (20 mL) was added to the mixture. The organic layer separated and was washed with water (10 mL), brine (10 mL), dried over anhydrous $Na_2SO_4$ and concentrated under vaccum. The crude product was further purified by prep-HPLC to afford Example 10 (6.7 mg, 0.010 mmol, 15.1% yield) as white gum. Ms calc'd 440 [(M+H)$^+$]; measured 440 [(M+H)$^+$]. $^1$H NMR (400 MHz, METHANOL-d$_4$) δ ppm: 9.41 (s, 1H), 7.90 (d, J=8.2 Hz, 1H), 7.14 (d, J=8.3 Hz, 1H), 4.19 (s, 1H), 4.03-3.94 (m, 1H), 3.73 (d, J=11.9 Hz, 2H), 3.25-2.88 (m, 10H), 2.83-2.68 (m, 5H), 1.91-1.58 (m, 8H), 1.31 (d, J=6.1 Hz, 3H).

Example 11

(2R,6R)-4-(4-cyano-1,3-benzothiazol-7-yl)-6-methyl-N-(1-methyl-4-piperidyl)morpholine-2-carboxamide

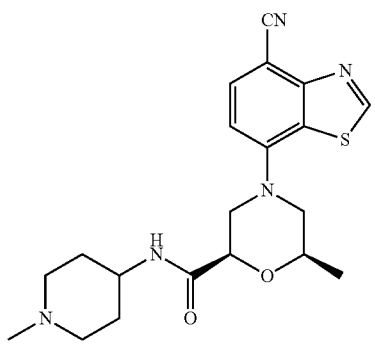 [SMILES: C[C@@H]1CN(c2ccc(C#N)c3ncsc23)C[C@H](C(=O)NC2CCN(C)CC2)O1]

The title compound was prepared according to the following scheme:

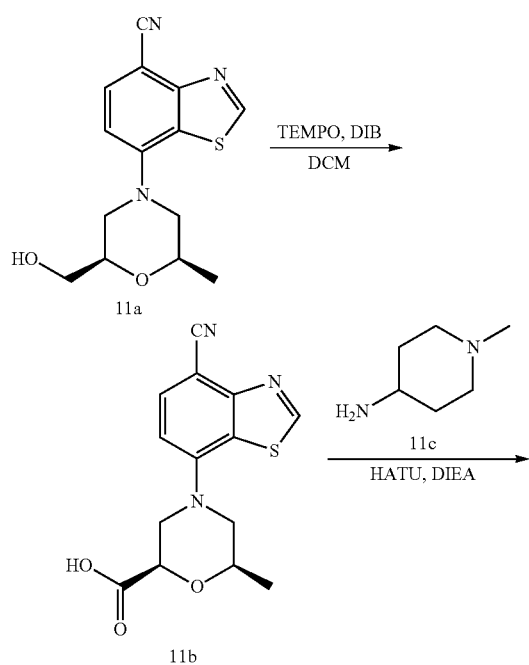

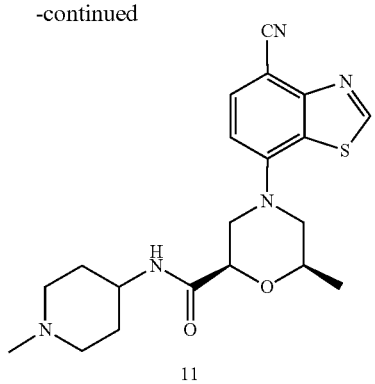

Step 1: Preparation of (2R,6R)-4-(4-cyano-1,3-benzothiazol-7-yl)-6-methyl-morpholine-2-carboxylic acid (Compound 11b)

To the solution of 7-[(2R,6R)-2-(hydroxymethyl)-6-methyl-morpholin-4-yl]-1,3-benzothiazole-4-carbonitrile (compound 11a, 20.0 mg, 0.07 mmol) in DCM (1.0 mL) and $H_2O$ (0.5 mL) was added benzoyl peroxide (45.0 mg, 0.14 mmol) and TEMPO (2.1 mg, 0.014 mmol). After the reaction mixture was stirred at 20° C. for 18 hrs, the pH of the mixture was adjusted to 3 by addition of HCl (1 M). The resultant mixture was extracted with EA (20 mL) and the aqueous phase was basified with a.q $NaHCO_3$ and extracted with EA (2×20 mL). The combined organic layers was concentrated under vaccum to afford compound 11b (15.0 mg, crude) as colorless oil. MS calc'd 304 [(M+H)$^+$]; measured 304 [(M+H)$^+$].

Step 2: Preparation of (2R,6R)-4-(4-cyano-1,3-benzothiazol-7-yl)-6-methyl-N-(1-methyl-4-piperidyl)morpholine-2-carboxamide (Example 11)

To the solution of (2R,6R)-4-(4-cyano-1,3-benzothiazol-7-yl)-6-methyl-morpholine-2-carboxylic acid (compound 11b, 15.0 mg, 0.050 mmol) in DMF (1.0 mL) was added N,N-diisopropylethylamine (20.0 mg, 0.15 mmol), HATU (28.0 mg, 0.075 mmol) and 1-methylpiperidin-4-amine (compound 11c, WuXi Apptec, 41838-46-4, 8 mg, 0.07 mmol). After the reaction mixture was stirred for 2 hrs at 25° C., it was diluted with EA (30 mL) and washed with brine (2×20 mL). The organic layer was separated, dried over $Na_2SO_4$, concentrated under vaccum and the residue was purified by prep-HPLC (FA) to afford Example 11 (3.2 mg, 16%) as a white solid. MS calc'd 400 [(M+H)$^+$]; measured 400 [(M+H)$^+$]. $^1$H NMR (400 MHz, METHANOL-d$_4$) δ ppm: 9.42 (s, 1H), 7.91 (d, J=8.3 Hz, 1H), 7.16 (d, J=8.2 Hz, 1H), 4.34 (dd, J=2.6, 10.8 Hz, 1H), 4.08-3.98 (m, 3H), 3.71 (d, J=12.3 Hz, 1H), 3.50 (d, J=11.2 Hz, 2H), 3.12 (t, J=11.2 Hz, 2H), 2.92-2.84 (m, 4H), 2.82-2.72 (m, 1H), 2.12 (s, 2H), 1.99-1.85 (m, 2H), 1.38 (d, J=6.3 Hz, 3H).

Example 12

(2R,6R)-4-(4-cyano-1,3-benzothiazol-7-yl)-6-methyl-N-[(4-methylmorpholin-2-yl)methyl]morpholine-2-carboxamide

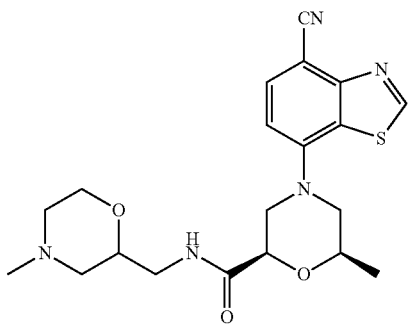 [SMILES: C[C@@H]1CN(c2ccc(C#N)c3ncsc23)C[C@H](C(=O)NCC2CN(C)CCO2)O1]

The title compound was prepared in analogy to the preparation of Example 11 by using (4-methylmorpholin-2-yl)methanamine (Bide, CAS: 141814-57-5) instead of 1-methylpiperidin-4-amine (compound 11c). Example 12 (11.9 mg, 23%) was obtained as a white solid. MS calc'd 416 [(M+H)$^+$]; measured 416 [(M+H)$^+$]. $^1$H NMR (400 MHz, METHANOL-d$_4$) δ ppm: 9.43 (s, 1H), 7.92 (d, J=8.2 Hz, 1H), 7.17 (d, J=8.3 Hz, 1H), 4.40-4.33 (m, 1H), 4.13-3.98 (m, 3H), 3.82-3.68 (m, 3H), 3.51-3.38 (m, 3H), 3.31-3.16 (m, 2H), 2.91-2.78 (m, 3H), 2.76 (s, 3H), 1.38 (d, J=6.4 Hz, 3H).

Example 13

The following tests were carried out in order to determine the activity of the compounds of formula (I) in HEK293-Blue-hTLR-7/8/9 cells assay.

HEK293-Blue-hTLR-7 Cells Assay:

A stable HEK293-Blue-hTLR-7 cell line was purchased from InvivoGen (Cat. #: hkb-htlr7, San Diego, Calif., USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR7 activation leads to downstream NF-κB activation has been widely accepted, and therefore similar reporter assay was modified for evaluating TLR7 antagonist.

HEK293-Blue-hTLR-8 Cells Assay:

A stable HEK293-Blue-hTLR-8 cell line was purchased from InvivoGen (Cat. #: hkb-htlr8, San Diego, Calif., USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR8 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR8 activation leads to downstream NF-κB activation has been widely accepted, and therefore similar reporter assay was modified for evaluating TLR8 antagonist.

HEK293-Blue-hTLR-9 Cells Assay:

A stable HEK293-Blue-hTLR-9 cell line was purchased from InvivoGen (Cat. #: hkb-htlr9, San Diego, Calif., USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, Calif., USA), for incubation of 20 hrs. The cell culture supernatant SEAP reporter activity was determined using QUANTI-Blue™ kit (Cat. #: rep-qb1, Invivogen, San Diego, Calif., USA) at a wavelength of 640 nm, a detection medium that turns purple or blue in the presence of alkaline phosphatase.

HEK293-Blue-hTLR9 cells were incubated at a density of 250,000450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM ODN2006 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR9 activation leads to downstream NF-κB activation has been widely accepted, and therefore similar reporter assay was modified for evaluating TLR9 antagonist.

The compounds of formula (I) have human TLR7 and/or TLR8 inhibitory activities (IC$_{50}$ value)<0.5 μM, particularly <0.020 μM. Moreover, some compounds also have human TLR9 inhibitory activity<1 μM, particularly <0.2 μM. Activity data of the compounds of the present invention were shown in Table 1.

TABLE 1

The activity of the compounds of present invention in HEK293-Blue-hTLR-7/8/9 cells assays

| Example | TLR7 IC$_{50}$ (μM) | TLR8 IC$_{50}$ (μM) | TLR9 IC$_{50}$ (μM) |
| --- | --- | --- | --- |
| 1 | 0.011 | <0.003 | 0.087 |
| 2 | 0.026 | 0.005 | 0.300 |
| 3 | 0.019 | 0.012 | 0.077 |
| 4 | 0.012 | 0.014 | 0.101 |
| 5 | 0.048 | 0.107 | 0.145 |
| 6 | 0.041 | 0.022 | 0.098 |
| 7 | 0.013 | <0.003 | 0.118 |
| 8 | 0.016 | <0.003 | 0.109 |
| 9 | 0.045 | 0.008 | 0.065 |
| 10 | 0.015 | <0.003 | 0.077 |
| 11 | 0.005 | <0.003 | 17.538 |
| 12 | 0.004 | <0.003 | 36.819 |

The invention claimed is:

1. A compound of formula (I),

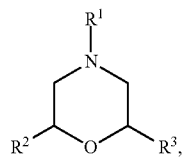

(I)

wherein:
R$^1$ is

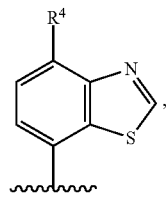

wherein R$^4$ is cyano, C$_{1-6}$alkyl, halogen, haloC$_{1-6}$alkyl or nitro;
R$^2$ is C$_{1-6}$alkyl, C$_{3-7}$cycloalkyl or haloC$_{1-6}$alkyl; and
R$^3$ is —C$_{1-6}$alkyl-R$^5$ or —CONR$^6$R$^7$, wherein:
R$^5$ is aminoazabicyclo[3.2.1]octanyl, aminopiperidinyl, C$_{1-6}$alkyldiazaspiro[5.5]undecanyl, diazaspiro[3.5]nonanyl, diazaspiro[4.5]decanyl, diazaspiro[5.5]undecanyl, piperidinylpiperidinyl, or 3-amino-8-azabicyclo[3.2.1]octan-8-yl;
R$^6$ is H; and
R$^7$ is C$_{1-6}$alkylpiperidinyl or C$_{1-6}$alkylmorpholinylC$_{1-6}$alkyl;

or a pharmaceutically acceptable salt, enantiomer or diastereomer thereof.

2. A compound according to claim 1, wherein:
R$^4$ is cyano; and
R$^2$ is C$_{1-6}$alkyl;
or a pharmaceutically acceptable salt, enantiomer or diastereomer thereof.

3. A compound according to claim 2, or a pharmaceutically acceptable salt, enantiomer or diastereomer thereof, wherein R$^3$ is —CH$_2$—R$^5$ or —CONR$^6$R$^7$.

4. A compound according to claim 3, or a pharmaceutically acceptable salt, enantiomer or diastereomer thereof, wherein R$^2$ is methyl.

5. A compound according to claim 1, or a pharmaceutically acceptable salt, enantiomer or diastereomer thereof, wherein R$^5$ is selected from: 2,8-diazaspiro[3.5]nonan-2-yl, 2,8-diazaspiro[4.5]decan-8-yl, 2,9-diazaspiro[4.5]decan-2-yl, 2,9-diazaspiro[5.5]undecan-9-yl, 2-methyl-2,9-diazaspiro[5.5]undecan-9-yl, 3,9-diazaspiro[5.5]undecan-3-yl, 3-amino-8-azabicyclo[3.2.1]octan-8-yl, 4-(1-piperidinyl)-1-piperidinyl, and 4-amino-1-piperidinyl.

6. A compound according to claim 5, or a pharmaceutically acceptable salt, enantiomer or diastereomer thereof, wherein R$^7$ is 1-methyl-4-piperidinyl or 4-methylmorpholin-2-ylmethyl.

7. A compound according to claim 2, selected from:
7-[(2S,6R)-2-(2,9-diazaspiro[4.5]decan-2-ylmethyl)-6-methyl-morpholin-4-yl]-1,3-benzothiazole-4-carbonitrile;
7-[(2S,6R)-2-[(4-amino-1-piperidyl)methyl]-6-methyl-morpholin-4-yl]-1,3-benzothiazole-4-carbonitrile;
7-[(2S,6R)-2-(2,9-diazaspiro[5.5]undecan-9-ylmethyl)-6-methyl-morpholin-4-yl]-1,3-benzothiazole-4-carbonitrile;
7-[(2S,6R)-2-(2,8-diazaspiro[3.5]nonan-2-ylmethyl)-6-methyl-morpholin-4-yl]-1,3-benzothiazole-4-carbonitrile;
7-[(2S,6R)-2-(3,9-diazaspiro[5.5]undecan-3-ylmethyl)-6-methyl-morpholin-4-yl]-1,3-benzothiazole-4-carbonitrile;
7-[(2S,6R)-2-(2,8-diazaspiro[4.5]decan-8-ylmethyl)-6-methyl-morpholin-4-yl]-1,3-benzothiazole-4-carbonitrile;
7-[(2R,6S)-2-methyl-6-[[4-(1-piperidyl)-1-piperidyl]methyl]morpholin-4-yl]-1,3-benzothiazole-4-carbonitrile;
Endo-7-[(2S,6R)-2-[[(1R,5S)-3-amino-8-azabicyclo[3.2.1]octan-8-yl]methyl]-6-methyl-morpholin-4-yl]-1,3-benzothiazole-4-carbonitrile;
Exo-7-[(2S,6R)-2-[[(1S,5R)-3-amino-8-azabicyclo[3.2.1]octan-8-yl]methyl]-6-methyl-morpholin-4-yl]-1,3-benzothiazole-4-carbonitrile;
7-[(2R,6S)-2-methyl-6-[(2-methyl-2,9-diazaspiro[5.5]undecan-9-yl)methyl]morpholin-4-yl]-1,3-benzothiazole-4-carbonitrile;
(2R,6R)-4-(4-cyano-1,3-benzothiazol-7-yl)-6-methyl-N-(1-methyl-4-piperidyl)morpholine-2-carboxamide;
(2R,6R)-4-(4-cyano-1,3-benzothiazol-7-yl)-6-methyl-N-[(4-methylmorpholin-2-yl)methyl]morpholine-2-carboxamide;

or a pharmaceutically acceptable salt, enantiomer or diastereomer thereof.

8. A process for preparing a compound according to claim 1 comprising any one of the following:
substituting a compound of formula (VII),

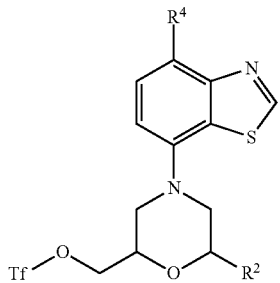
(VII)

with an amine in the presence of a base; or
reacting a compound of formula (VIII),

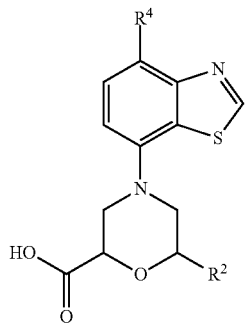
(VIII)

(IX)

with amine (IX) in the presence of a coupling reagent;
wherein:
Tf is trifluoromethansulfonyl;
the base is $Cs_2CO_3$; and
the coupling reagent is HATU.

9. A pharmaceutical composition comprising a compound in accordance with claim 1, or a pharmaceutically acceptable salt, enantiomer or diastereomer thereof, and a therapeutically inert carrier.

10. A method for inhibiting TLR7, TLR8, or TLR9, or any combination thereof, in a patient in need thereof, which method comprises:
administering a therapeutically effective amount of a compound as defined in claim 1, or a pharmaceutically acceptable salt, enantiomer or diastereomer thereof, to the patient in need thereof.

11. A pharmaceutical composition comprising a compound in accordance with claim 7, or a pharmaceutically acceptable salt, enantiomer or diastereomer thereof, and a therapeutically inert carrier.

12. A method for inhibiting TLR7, TLR8, or TLR9, or any combination thereof, in a patient in need thereof, which method comprises administering a therapeutically effective amount of a compound of claim 7, or a pharmaceutically acceptable salt, enantiomer or diastereomer thereof, to the patient in need thereof.

* * * * *